United States Patent [19]
Yamamoto et al.

[11] 4,355,193
[45] Oct. 19, 1982

[54] METHOD FOR THE PREPARATION OF CIS-NONEN-6-YL CHLORIDE

[75] Inventors: Akira Yamamoto; Toshinobu Ishihara; Kenichi Taguchi, all of Joetsu, Japan

[73] Assignee: Shin-Etsu Chemical Co., Ltd., Tokyo, Japan

[21] Appl. No.: 253,061

[22] Filed: Apr. 10, 1981

[30] Foreign Application Priority Data

Apr. 14, 1980 [JP] Japan ............................. 55-48935

[51] Int. Cl.³ ............................................. C07C 17/26
[52] U.S. Cl. ................................................... 570/217
[58] Field of Search ........................................ 570/217

[56] References Cited
U.S. PATENT DOCUMENTS 3,033,884  5/1962  Osbond et al. ...................... 570/217

Primary Examiner—Charles F. Warren
Assistant Examiner—Joseph A. Boska
Attorney, Agent, or Firm—Toren, McGeady & Stanger

[57] ABSTRACT

The invention provides a novel and efficient method for the synthetic preparation of cis-nonen-6-yl chloride which is a useful intermediate compound for the syntheses of, for example, cis-nonen-6-yl acetate, cis-nonen-6-ol, cis-nonen-6-al and the like as flavors as well as cis-dodecen-9-yl acetate and cis-tetradecen-11-yl acetate known as sexual pheromone compounds of several noxious insects. The inventive method comprises reacting 1-bromo-3-chloropropane with the Grignard reagent of cis-hexen-3-yl chloride which is a chlorination product of cis-hexen-3-ol known by a trivial name of leaf alcohol. The reaction is preferably carried out in tetrahydrofuran in the presence of a catalyst which may be lithium copper dichloride or dilithium copper tetrachloride at 0° to 40° C.

5 Claims, No Drawings

METHOD FOR THE PREPARATION OF CIS-NONEN-6-YL CHLORIDE

BACKGROUND OF THE INVENTION

The present invention relates to a novel method for the synthetic preparation of cis-nenen-6-yl chloride.

Cis-nonen-6-yl chloride is a useful compound as an intermediate for the synthesis of cis-nonen-6-yl acetate, cis-nonen-6-ol, cis-nonen-6-al and the like known as flavors having melon-like or cucumber-like odors. It is also useful as an intermediate compound for the synthesis of cis-dodecen-9-yl acetate, cis-tetradecen-11-yl acetate and the like known as sexual pheromone compounds of grape berry moth, tea tortrix, summer fruit tortrix and the like noxious insects to provide a promising means for the extermination of these noxious insects in the fields.

In the prior art, unfortunately, there is known no economically advantageous method for the preparation of this cis-nonen-6-yl chloride with low costs.

SUMMARY OF THE INVENTION

Thus, it is an object of the present invention to provide a novel and economically advantageous method for the synthetic preparation of cis-nonen-6-yl chloride.

The method of the present invention for the synthetic preparation of cis-nonen-6-yl chloride comprises reacting the Grignard reagent of cis-hexen-3-yl chloride with 1-bromo-3-chloropropane. The reaction is preferably carried out in tetrahydrofuran as the solvent in the presence of lithium copper dichloride or dilithium copper tetrachloride as a catalyst to give the desired compound in a yield as high as 85% to 90% of the theoretical value.

DETAILED DESCRIPTION OF THE PREFERRED EMBODIMENTS

One of the reactants to be cross-coupled in the reaction of the invention is the Grignard reagent of cis-hexen-3-yl chloride which in turn is readily obtained by the chlorination reaction of cis-hexen-3-ol, which is known by a trivial name of leaf alcohol, with a chlorinating agent such as thionyl chloride in a conventional manner in a yield of 85 to 90% of the theoretical.

The Grignard reagent of cis-hexen-3-yl chloride, i.e. cis-hexen-3-yl magnesium chloride, is readily obtained by reacting this chloride with metallic magnesium in tetrahydrofuran at a temperature from 40° to 66° C.

The other reactant used in the reaction of the inventive method is 1-bromo-3-chloropropane, which is added dropwise to the above described tetrahydrofuran solution of cis-hexen-3-yl magnesium chloride under agitation and kept at a temperature of 0° to 40° C., whereupon the cross coupling reaction takes place between the Grignard reagent and 1-bromo-3-chloropropane to give the desired cis-nonen-6-yl chloride in a yield of 85 to 90% of the theoretical.

In carrying out the above cross coupling reaction, the molar ratio of the amounts of the reactants to be taken should approximately be equimolar. The cross coupling reaction is preferably accelerated by adding lithium copper dichloride $LiCuCl_2$ or dilithium copper tetrachloride $Li_2CuCl_4$ as a catalyst to the reaction mixture.

The above mentioned lithium copper dichloride or dilithium copper tetrachloride is readily formed when lithium chloride is admixed in tetrahydrofuran with copper (I) chloride in a proportion of 1:1 by moles or with copper (II) chloride in a proportion of 2:1 by moles as a solution of the catalyst in tetrahydrofuran, respectively. The catalyst solution may be added to the tetrahydrofuran solution of the Grignard reagent in advance. The amount of the catalyst to be used in the reaction is in the range from 0.001 mole to 0.1 mole or, preferably, from 0.003 mole to 0.02 mole per mole of the Grignard reagent for each of the lithium-copper dichloride and dilithium copper tetrachloride.

The amount of tetrahydrofuran used as the solvent should be at least equimolar to the magnesium used for the preparation of the Grignard reagent or, preferably, from 3 to 20 moles per mole of the metallic magnesium.

After completion of the cross coupling reaction, the reaction mixture is filtered or washed with water to remove the salts as the by-products. Thereafter, tetrahydrofuran is stripped away from the reaction mixture, which is then subjected to distillation to give a fraction of the desired cis-nonen-6-yl chloride in a yield of 85 to 90% of the theoretical value.

Cis-nonen-6-yl chloride as the objective compound of the inventive method can readily be converted to valuable flavors such as cis-nonen-6-yl acetate, cis-nonen-6-ol, cis-nonen-6-al and the like and also is useful as an intermediate for the synthesis of cis-tetradecen-11-yl acetate and the like compounds known as sexual pheromone compounds of several noxious insects.

The inventive method is described in further detail by way of an example.

EXAMPLE

Into a reaction vessel of 2 liter capacity were taken 24.3 g of metallic magnesium, 360 g of anhydrous tetrahydrofuran and a bit of iodine to form a reaction into which 2 g of ethyl bromide were added dropwise with agitation. While keeping the reaction mixture at 50° C., 118.5 g of cis-hexen-3-yl chloride were added dropwise into the reaction mixture over a period of 2 hours to form a Grignard reagent thereof. After the end of the addition of cis-hexen-3-yl chloride, agitation of the reaction mixture was further continued for additional 1 hour to complete the reaction followed by cooling to 20° C.

A tetrahydrofuran solution of dilithium copper tetrachloride $Li_2CuCl_4$ separately prepared by dissolving 0.430 g of lithium chloride and 0.676 g of copper (II) chloride in 100 g of tetrahydrofuran was added into the reaction mixture and, while keeping the reaction mixture at a temperature of 15° to 20° C. by cooling from outside with ice, 158 g of 1-bromo-3-chloropropane were added thereto dropwise with agitation to effect the reaction over a period of about 2 hours. After the end of the addition of 1-bromo-3-chloropropane, the temperature of the reaction mixture was increased to 40° C. where the reaction was completed by keeping the reaction mixture at the temperature followed by cooling to room temperature. The precipitated salts and the catalyst in the reaction mixture were removed by filtering. The reaction mixture was then subjected to stripping off of tetrahydrofuran as the solvent and distillation under reduced pressure to give 128 g of cis-nonen-6-yl chloride as a clear and colorless liquid fraction. The yield was about 84% of the theoretical value.

What is claimed is:

1. A method for the preparation of cis-nonen-6-yl chloride which comprises reacting the Grignard reagent of cis-hexen-3-yl chloride with 1-bromo-3-chloropropane in the presence of a catalyst selected from the group consisting of lithium copper dichloride and dilithium copper tetrachloride.

2. The method as claimed in claim 1 wherein the reaction of the Grignard reagent of cis-hexen-3-yl chloride and 1-bromo-3-chloropropane is carried out in tetrahydrofuran in the presence of a catalyst selected from the group consisting of lithium copper dichloride and dilithium copper tetrachloride.

3. The method as claimed in claim 2 wherein the reaction is carried out at a temperature in the range from 0° to 40° C.

4. The method as claimed in claim 2 wherein the amount of the catalyst is in the range from 0.001 mole to 0.1 mole per mole of the Grignard reagent.

5. The method as claimed in claim 2 wherein the amount of the tetrahydrofuran is in the range from 3 to 20 moles per mole of the Grignard reagent.

* * * * *